(12) United States Patent
Otsuka et al.

(10) Patent No.: US 9,080,964 B2
(45) Date of Patent: Jul. 14, 2015

(54) GAS SENSOR ELEMENT AND GAS SENSOR (71) Applicant: NGK SPARK PLUG CO., LTD., Nagoya-shi, Aichi (JP)

(72) Inventors: Sigehiro Otsuka, Gifu (JP); Masaki Onkawa, Komaki (JP); Toru Iwano, Komaki (JP); Satoshi Teramoto, Nisshin (JP); Kuniharu Tanaka, Komaki (JP); Takeshi Mitsuoka, Konan (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 273 days.

(21) Appl. No.: 13/665,731

(22) Filed: Oct. 31, 2012

(65) Prior Publication Data

US 2013/0104625 A1    May 2, 2013

(30) Foreign Application Priority Data

Oct. 31, 2011    (JP) .................................. 2011-238736

(51) Int. Cl.
*G01N 27/407*    (2006.01)
*G01N 33/00*    (2006.01)

(52) U.S. Cl.
CPC ........ *G01N 27/4077* (2013.01); *G01N 33/0014* (2013.01); *G01N 33/0037* (2013.01)

(58) Field of Classification Search
CPC ............ G01N 27/125; G01N 33/0037; G01N 33/0014
See application file for complete search history.

(56) References Cited

U.S. PATENT DOCUMENTS

| 7,329,844 | B2 | 2/2008 | Kojima et al. | |
| 2003/0159928 | A1 | 8/2003 | Kojima et al. | |
| 2004/0026265 | A1* | 2/2004 | Nadanami et al. | 205/775 |
| 2007/0000780 | A1* | 1/2007 | Oya et al. | 204/424 |

FOREIGN PATENT DOCUMENTS

| JP | 2003-322632 A | 11/2003 |
| JP | 2007-206082 A | 8/2007 |

* cited by examiner

*Primary Examiner* — Paul West
(74) *Attorney, Agent, or Firm* — Sughrue Mion, PLLC (57) ABSTRACT

A gas sensor element (100) includes a laminate of a detection element (300) and a heater (200), and a porous protection layer (20) covering a forward end portion thereof. The laminate has a measuring chamber (107c) into which a gas-to-be-measured is introduced via a diffusion resistor (115). The porous protection layer includes an inner porous layer (21), and an outer porous layer (23). The inner porous layer has a higher porosity than the outer porous layer and the diffusion resistor. As viewed in a plurality of 100 μm×100 μm regions $a_1$ to $a_3$ and $b_1$ to $b_3$ on sections of the inner porous layer and the diffusion resistor, respectively, a pore diameter greater than the greatest pore diameter $C_{DIF}$ in the regions of the diffusion resistor exists in each of the regions of the inner porous layer.

10 Claims, 8 Drawing Sheets

TOTAL THICKNESS OF POROUS PROTECTION LAYER (μm)

GAS SENSOR ELEMENT AND GAS SENSOR

BACKGROUND OF THE INVENTION

1. Field of the Invention

The present invention relates to a gas sensor element and a gas sensor adapted for detecting the concentration of a particular gas contained in, for example, combustion gas or exhaust gas of a combustor, an internal combustion engine, etc.

2. Description of the Related Art

Conventionally, a gas sensor is used for detecting the concentration of a particular component (oxygen, etc.) in exhaust gas of an internal combustion engine. The gas sensor has a gas sensor element provided therein. The gas sensor element comprises a laminate of a detection element and a heater. The detection element has at least one cell composed of a solid electrolyte body and a pair of electrodes disposed on the solid electrolyte body. The heater has an insulating ceramic body and a heat-generating element provided in the insulating ceramic body and is adapted to generate heat by passing electric current therethrough. Meanwhile, the gas sensor element may be exposed to poisoning substances, such as silicon and phosphorus, contained in exhaust gas and may be subjected to adhesion of water droplets contained in exhaust gas. Thus, in order to trap poisoning substances and to prevent direct contact of water droplets with the gas sensor element, the outer surface of the gas sensor element is covered with a porous protection layer. That is, in the laminate, a forward end portion that is exposed to a gas-to-be-measured is entirely covered with the porous protection layer.

Also, the following technique has been developed: the porous protection layer consists of two layers; namely, an upper layer and a lower layer. By means of the lower layer having a porosity higher than that of the upper layer, an anchor effect brings the upper layer into close contact with the lower layer, whose surface is roughened by pores (refer to Patent Documents 1 and 2).

The above-mentioned laminate has a measuring chamber which one of the above-mentioned pair of electrodes faces. The gas-to-be-measured is introduced into the measuring chamber. A diffusion resistor intervenes between the measuring chamber and the ambient atmosphere and is adapted to adjust the diffusion rate of the gas-to-be-measured into the measuring chamber. Thus, the lower layer is in direct contact with the diffusion resistor.

PATENT DOCUMENTS

[Patent Document 1] Japanese Patent Application Laid-Open (kokai) No. 2003-322632 (claim 15)
[Patent Document 2] Japanese Patent Application Laid-Open (kokai) No. 2007-206082 (claim 15)

Problems to be Solved by the Invention

By employing a porous protection layer having a two-layer structure such that the lower layer has a higher porosity than the upper layer, the total volume of voids (empty spaces) contained in the lower layer increases, thereby imparting thermal insulation properties to the lower layer. Therefore, even when the upper layer is cooled by adhesion of water, the gas sensor element which is disposed inside of the upper layer is unlikely to be suddenly cooled. Even in a state in which the heater heats the detection element, damage to the gas sensor element caused by adhesion of water can be effectively restrained.

Figure 9A:
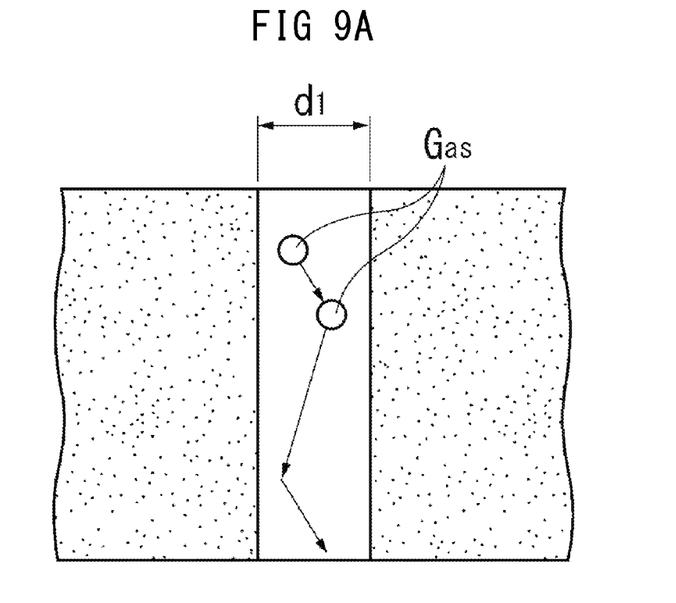
FIGS. 9A and 9B are views schematically showing the relation between a pore diameter in a porous protection layer and a state of diffusion of gas.
Figure 9B:
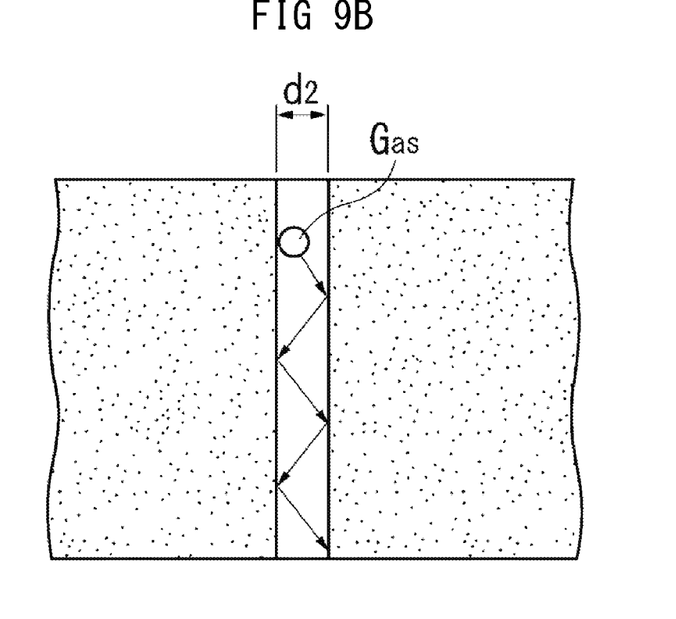

Meanwhile, the diffusion rate of a gas which passes through the porous protection layer depends not only on the porosity of the porous protection layer but also the pore diameter. For example, as shown in FIG. 9A, in the case of a large pore diameter $d_1$, a plurality of gas molecules $G_{as}$ simultaneously enters the pore and diffuses therein while colliding with one another (molecular diffusion). Therefore, diffusion resistance becomes low, and thus the diffusion rate increases as compared with fine-pore diffusion, which is described below. By contrast, as shown in FIG. 9B, in the case of a small pore diameter $d_2$, a plurality of the gas molecules $G_{as}$ fails to simultaneously enter the pore, and the gas molecules $G_{as}$ individually enter the pore and diffuse therein while impinging on the pore wall (fine-pore diffusion). Therefore, diffusion resistance becomes high, and thus the diffusion rate is lowered as compared with molecular diffusion.

Figure 10:
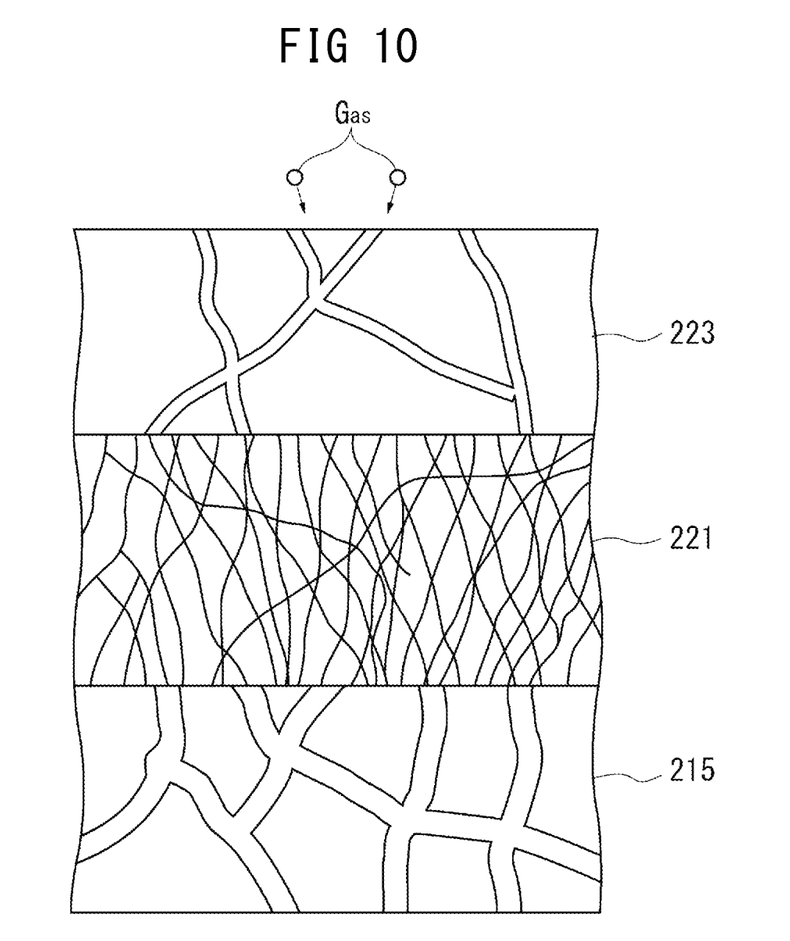
FIG. 10 is a view schematically showing an example configuration in which a large number of fine pores are formed in a lower layer adjacent to a diffusion resistor, whereas a small number of large pores are formed in an upper layer.

Thus, for example, in the case where, as shown in FIG. 10, a lower layer 221 adjacent to a diffusion resistor 215 has a large number of fine pores each having a pore diameter $d_2$, whereas an upper layer 223 has a small number of large pores each having a pore diameter $d_1$, the porosity of the lower layer 221 becomes higher than that of the upper layer 223, but the gas diffusion rate in the lower layer 221 is greatly reduced.

Figure 11:
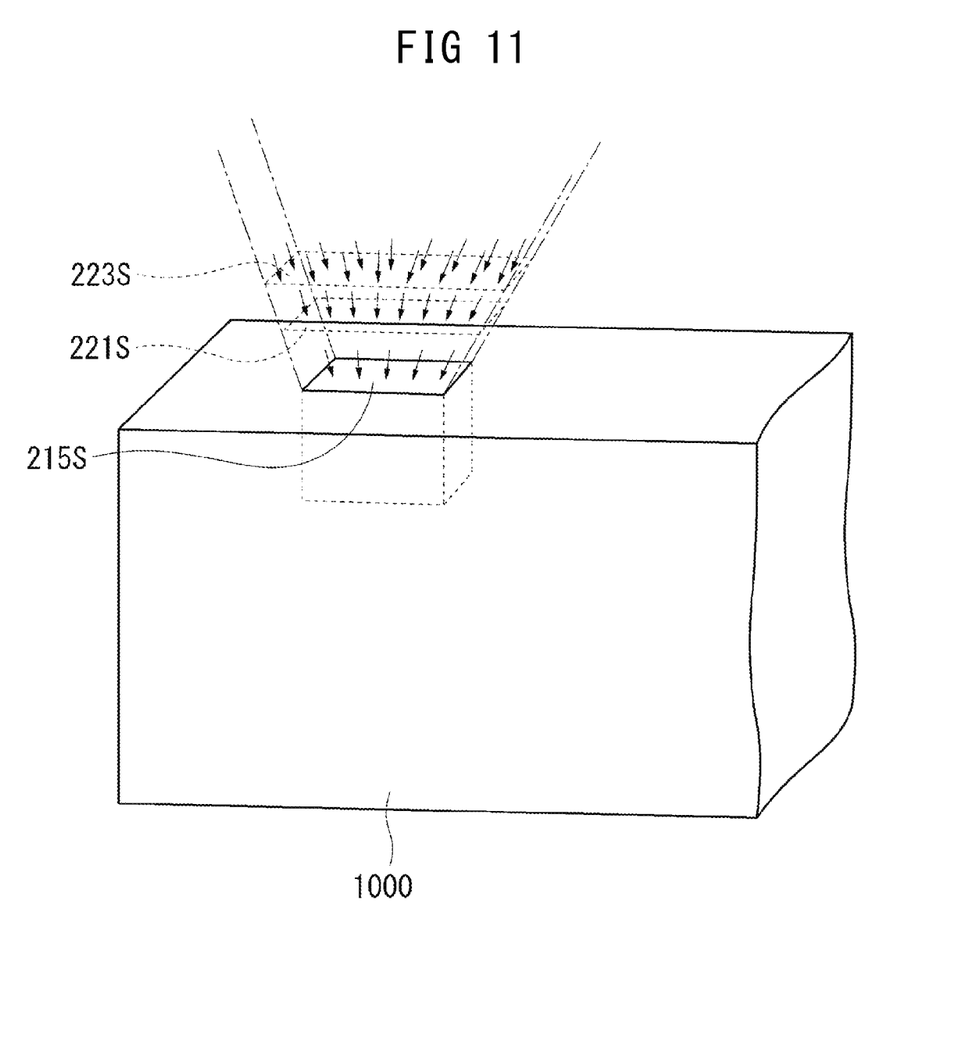
FIG. 11 is a view schematically showing a gas penetration path (gas passage area) from the ambient atmosphere to a gas sensor element.

Furthermore, as shown in FIG. 11, a gas penetration path (gas passage area) from the ambient atmosphere to a gas sensor element 1000 becomes narrower (smaller) toward the diffusion resistor 215. For example, in the case of FIG. 11, a gas passage area 215s on the surface of the diffusion resistor 215 is the smallest; a gas passage area 221s on the surface of the lower layer 221 is the next smallest; and a gas passage area 223s on the surface of the upper layer 223 is the greatest.

Accordingly, when the gas diffusion rate in the lower layer 221 adjacent to the diffusion resistor 215 is decreased, a gas encounters difficulty in diffusing (being introduced) into the measuring chamber, resulting in deteriorated sensor output.

SUMMARY OF THE INVENTION

In view of the foregoing, an object of the present invention is to provide a gas sensor element which resists cracking caused by adhesion of water and deterioration in sensor output, as well as a gas sensor employing the gas sensor element.

The above object of the present invention has been achieved by providing a gas sensor element which comprises a laminate of a detection element and a heater, and a porous protection layer which entirely covers a forward end portion of the laminate. The detection element has at least one cell composed of a solid electrolyte body and a pair of electrodes disposed on the solid electrolyte body. The heater has an insulating ceramic body and a heat-generating element provided in the insulating ceramic body and is adapted to generate heat by passing electric current therethrough. The laminate has a measuring chamber which is formed in its forward end portion, into which a gas-to-be-measured is introduced from an ambient atmosphere via a diffusion resistor, and which one of the pair of electrodes faces. In the gas sensor element, the porous protection layer comprises an inner porous layer disposed externally of the diffusion resistor and covering at least the diffusion resistor, and an outer porous layer formed externally of the inner porous layer and entirely covering the forward end portion of the laminate; the inner porous layer has a higher porosity than the outer porous layer; the inner porous layer has a higher porosity than the diffusion resistor; and, as viewed in a plurality of 100 µm×100 µm regions on a scanning electron micrograph of sections of the inner porous layer and the diffusion resistor, a pore diameter greater than a greatest pore diameter $C_{DIF}$ in the regions of the diffusion resistor exists in each of the regions of the inner porous layer.

In this manner, by means of the inner porous layer having a porosity higher than that of the outer porous layer, the gas diffusion rate can be readily increased in the inner porous layer, which is adjacent to the diffusion resistor and has the narrowest gas penetration path (gas passage area) for introducing a gas from the ambient atmosphere into the measuring chamber.

Also, by means of the outer porous layer having a porosity lower than that of the inner porous layer, the outer porous layer having a reduced porosity effectively traps poisoning substances and water droplets; thus, poisoning substances and water are unlikely to reach the laminate. Furthermore, by means of the inner porous layer having a porosity higher than that of the outer porous layer, the total volume of voids (empty spaces) contained in the inner porous layer is increased, thereby imparting thermal insulation properties to the inner porous layer. Therefore, even when the outer porous layer is cooled by adhesion of water, the laminate located on the inner side is unlikely to be suddenly cooled. Even in a state in which the heater heats the detection element, damage to the gas sensor element caused by adhesion of water can be effectively restrained.

Also, by means of the inner porous layer having a porosity higher than that of the diffusion resistor, the gas introduced from the ambient atmosphere readily flows through the inner porous layer toward the diffusion resistor.

Furthermore, the gas diffusion resistance of the porous protection layer depends to a large degree not only on porosity but also pore diameter. By providing of a pore diameter greater than the greatest pore diameter $C_{DIF}$ in the diffusion resistor in each of the regions of the inner porous layer, large-diameter pores (pores which allow for molecular diffusion, which is faster than fine-pore diffusion) reliably exist (i.e., are reliably present) in the inner porous layer. Accordingly, the gas diffusion resistance of the inner porous layer is reliably reduced, thereby facilitating diffusion (introduction) of gas into the measuring chamber. Thus, deterioration in sensor output can be restrained. The expression "a pore diameter greater than the greatest pore diameter $C_{DIF}$ in the diffusion resistor exists in each of the regions of the inner porous layer" indicates that at least one (preferably, more than one) pore diameter greater than the pore diameter $C_{DIF}$ exists in each of the regions of the inner porous layer.

No particular limitation is imposed on the configuration of the inner porous layer, so long as the inner porous layer is disposed externally of the diffusion resistor and covers at least the diffusion resistor. That is, the inner porous layer may be provided locally so as to cover the diffusion resistor and its vicinity, or may be provided so as to entirely cover a forward end portion of the laminate. In the present invention, the inner porous layer which partially constitutes the porous protection layer is a layer disposed adjacent or contiguous to the diffusion resistor. A gap may be provided between the inner porous layer and the diffusion resistor; however, preferably, the inner porous layer is provided adjacent to the diffusion resistor (i.e., the inner porous layer is provided directly on the surface of the laminate). No particular limitation is imposed on the configuration of the outer porous layer, so long as the outer porous layer is provided on or covers the inner porous layer. The porous protection layer may be constituted by only two layers; namely, the inner porous layer and the outer porous layer. However, the porous protection layer may be composed of three or more layers.

Furthermore, preferably, a pore diameter greater than the greatest pore diameter $C_{DIF}$ in the diffusion resistor does not exist in each of a plurality of 100 μm×100 μm regions on a scanning electron micrograph of the section of the outer porous layer. This feature allows the outer porous layer to effectively trap poisoning substances and water droplets. Although the outer porous layer has a relatively high diffusion resistance, since the gas penetration path expands with an outward distance from the diffusion resistor, gas can pass through the outer porous layer. Meanwhile, in order to allow sufficient passage of gas in the outer porous layer, one or more pore diameters greater than the greatest pore diameter $C_{DIF}$ in the diffusion resistor may exist in some or each of a plurality of the regions in the outer porous layer.

In a preferred embodiment, the inner porous layer entirely covers the forward end portion of the laminate.

According to the thus-configured gas sensor element, the inner porous layer has a higher porosity than the outer porous layer. As a result, by entirely covering the forward end portion of the laminate, the total volume of voids in the inner porous layer, which is located on a side toward the laminate, further increases, thereby further enhancing thermal insulation performance. Therefore, even when the outer porous layer is cooled by adhesion of water, the gas sensor element is unlikely to be suddenly cooled. Therefore, even in a state in which the heater heats the detection element, damage to the gas sensor element caused by adhesion of water can be more effectively suppressed.

In yet another preferred embodiment, the gas sensor element is an $NO_x$ sensor element comprising a first pump cell and a second pump cell. The first pump cell has a pair of first electrodes disposed on a first solid electrolyte layer and located internally and externally of a first measuring chamber, and is adapted to pump oxygen into and out of the gas-to-be-measured that has been introduced into the first measuring chamber. The second pump cell has a pair of second electrodes provided on a second solid electrolyte layer and located internally and externally of an $NO_x$ measuring chamber in communication with the first measuring chamber. In the second pump cell, a second pumping current flows between the pair of second electrodes according to an $NO_x$ concentration in a gas having an adjusted oxygen concentration and flowing from the first measuring chamber into the $NO_x$ measuring chamber. The aforementioned cell may be the first pump cell, and the aforementioned measuring chamber may be the first measuring chamber.

Since the $NO_x$ sensor has a lower sensor output as compared with a gas sensor for detecting oxygen concentration, $NO_x$ sensor output is more susceptible to obstruction in diffusion (introduction) of gas into the measuring chamber as compared with an oxygen gas sensor. Thus, the present invention is more effectively applied to an $NO_x$ sensor by providing the inner porous layer and the outer porous layer on the surface of the laminate having a diffusion resistor.

In a second aspect, the present invention provides a gas sensor which comprises the above described sensor element for detecting concentration of a particular gas component in a gas-to-be-measured, and a housing for holding the sensor element.

Effect of the Invention

The present invention can suppress cracking of the gas sensor element caused by adhesion of water and restrain deterioration in sensor output.

DESCRIPTION OF REFERENCE NUMERALS

Reference numerals used to identify various features in the drawings include the following.
1: gas sensor
20: porous protection layer
21, 21B, 21C: inner porous layer
23, 23B, 23C: outer porous layer
30: housing
104, 106, 108, 110, 104C, 106C, 108C, 110C: a pair of electrodes
106, 108, 106C, 108C: one of a pair of electrodes
107c, 107c2: measuring chamber
105, 105C, 109, 109C: solid electrolyte body
100, 100B, 100C: gas sensor element
115, 115C: diffusion resistor
200, 200C: heater
300, 300C: detection element
L: direction of axis
$a_1$ to $a_3$, $b_1$ to $b_3$: 100 µm×100 µm region

DETAILED DESCRIPTION OF THE PREFERRED EMBODIMENTS

Embodiments of the present invention will next be described with reference to the drawings. However, the present invention should not be construed as being limited thereto.

Figure 1:
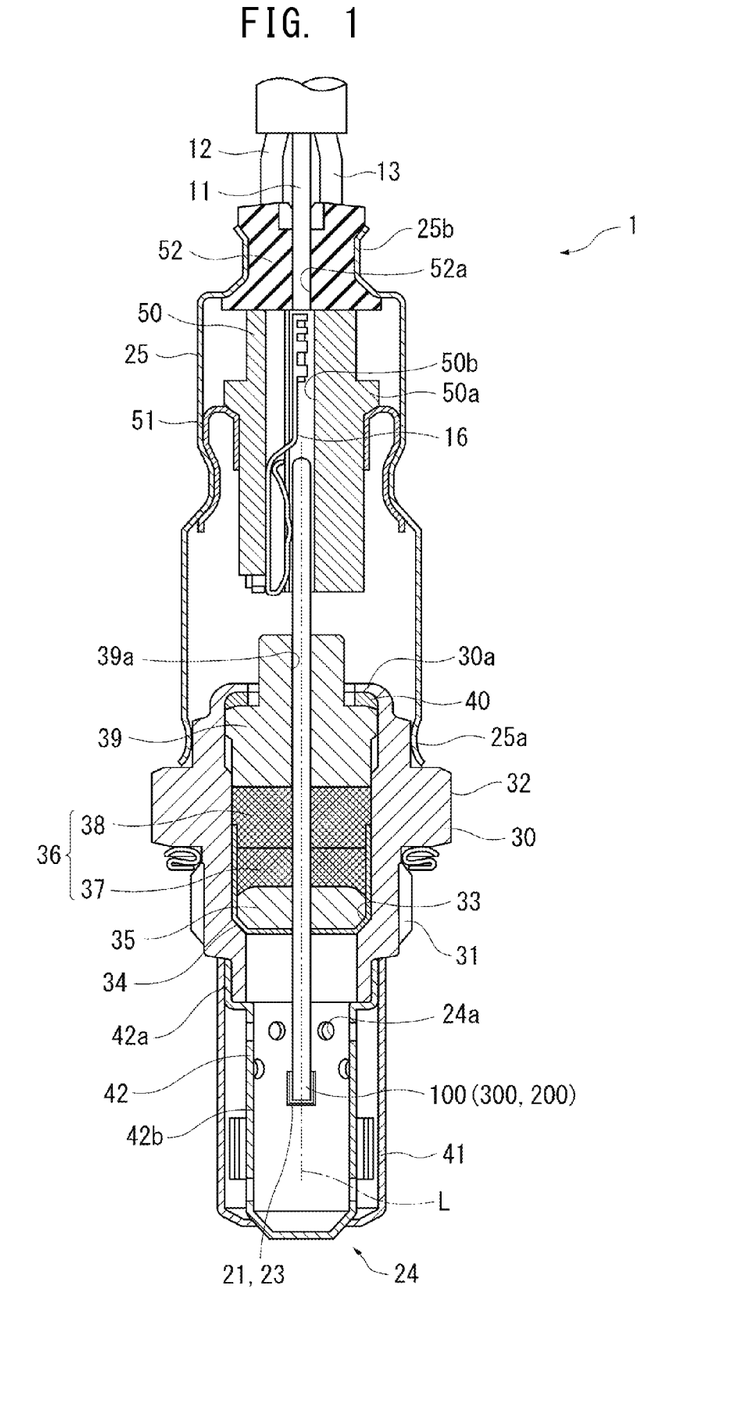
FIG. 1 is a sectional view of a gas sensor (oxygen sensor) according to a first embodiment of the present invention, taken along the longitudinal direction of the gas sensor.
Figure 2:
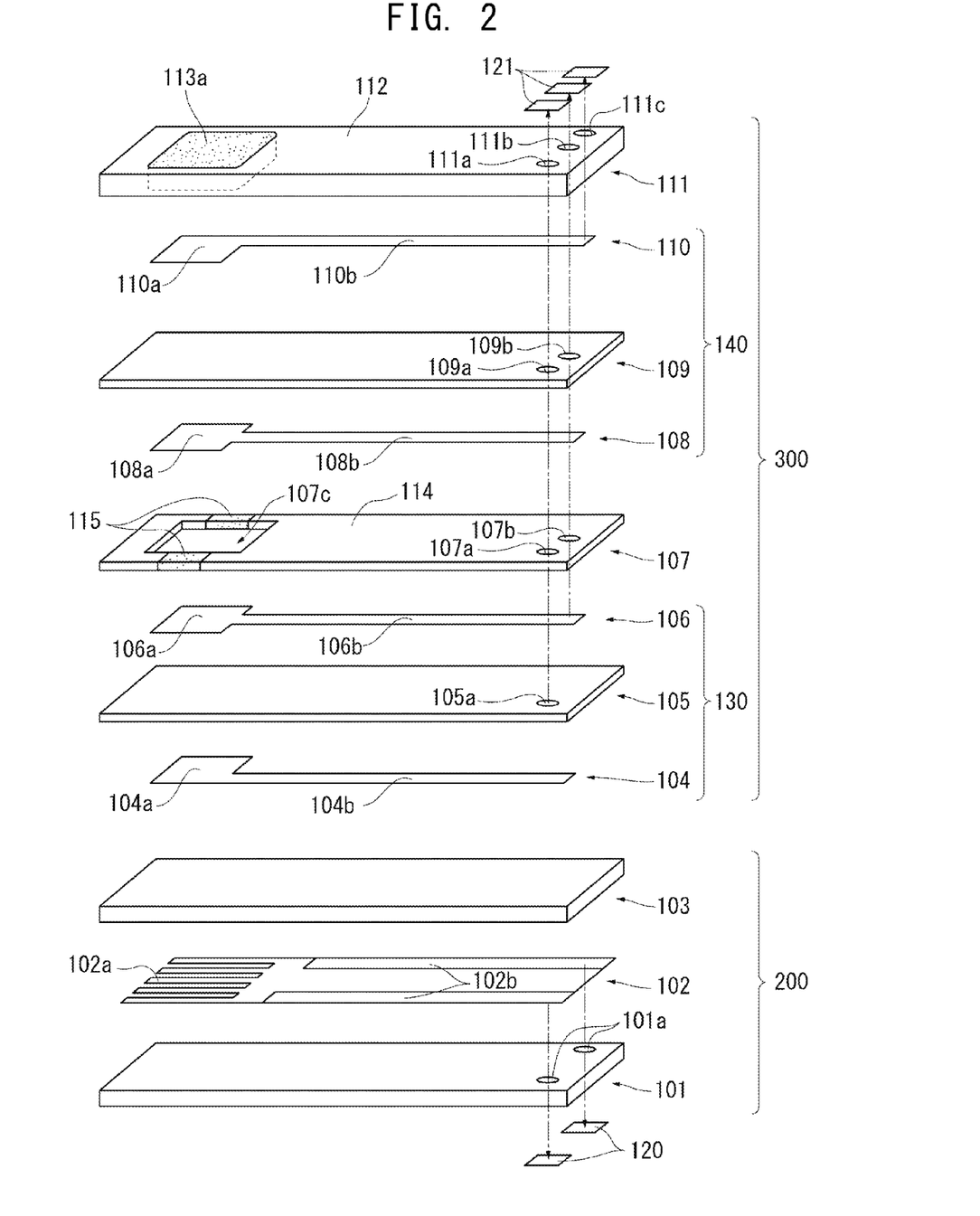
FIG. 2 is a schematic, exploded perspective view showing a detection element and a heater.
Figure 3:
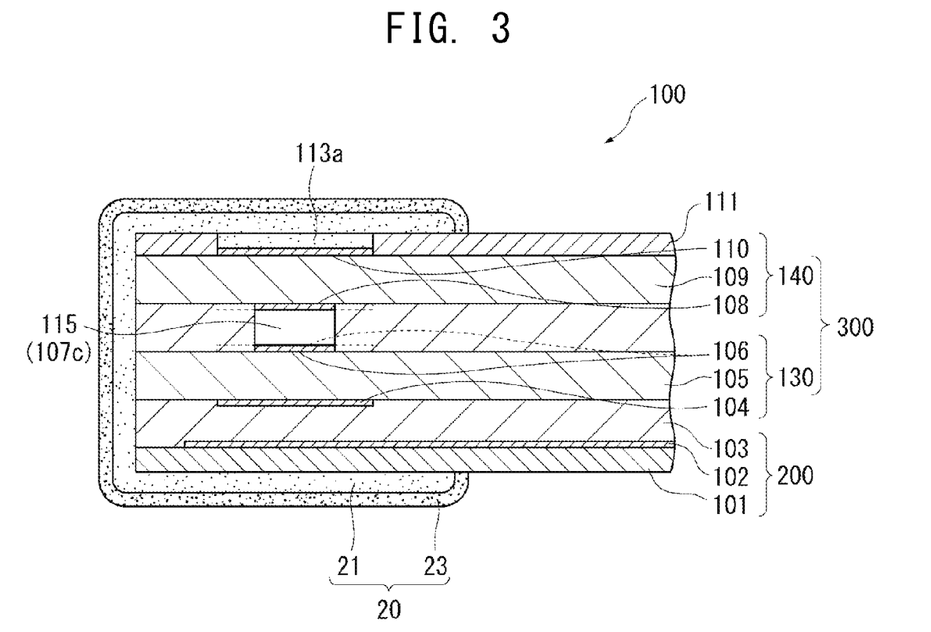
FIG. 3 is a fragmentary, enlarged sectional view showing a forward end portion of the detection element of FIG. 1.

FIG. 1 is a sectional view of a gas sensor (oxygen sensor) 1 according to a first embodiment of the present invention, taken along the longitudinal direction of the gas sensor (the direction of an axis L). FIG. 2 is a schematic, exploded perspective view showing a detection element 300 and a heater 200. FIG. 3 is a sectional view of the detection element 300 taken orthogonally to the direction of the axis L.

As shown in FIG. 1, the gas sensor 1 includes a gas sensor element 100 composed of the detection element 300 and the heater 200 laminated on the detection element 300; a metallic shell (corresponding to the "housing" of the invention) 30 for holding the gas sensor element 100, etc., therein; and a protector 24 attached to a forward end portion of the metallic shell 30. The gas sensor element 100 is disposed in such a manner as to extend in the direction of the axis L.

As shown in FIG. 2, the heater 200 includes a first substrate 101 and a second substrate 103, which predominantly contain alumina, and a heat-generating element 102, which is sandwiched between the first substrate 101 and the second substrate 103 and which heat-generating element 102 predominantly contains platinum. The heat-generating element 102 has a heat-generating portion 102a located at the forward end thereof and a pair of heater lead portions 102b extending from the heat-generating portion 102a along the longitudinal direction of the first substrate 101. The ends of the heater lead portions 102b are electrically connected to corresponding heater-side pads 120 via conductors formed in heater-side through holes 101a provided in the first substrate 101. A laminate of the first substrate 101 and the second substrate 103 corresponds to the "insulating ceramic body" of the invention.

The detection element 300 includes an oxygen concentration detection cell 130 and an oxygen pump cell 140. The oxygen concentration detection cell 130 includes a first solid electrolyte body 105, and a first electrode 104 and a second electrode 106, which are formed on respective opposite sides of the first solid electrolyte body 105. The first electrode 104 includes a first electrode portion 104a and a first lead portion 104b extending from the first electrode portion 104a along the longitudinal direction of the first solid electrolyte body 105. The second electrode 106 includes a second electrode portion 106a and a second lead portion 106b extending from the second electrode portion 106a along the longitudinal direction of the first solid electrolyte body 105.

Each of the oxygen concentration detection cell 130 and the oxygen pump cell 140 corresponds to the "cell" of the invention. Also, each of the second electrode 106 and a third electrode 108, described below, corresponds to "one of the pair of electrodes" of the invention.

The end of the first lead portion 104b is electrically connected to a corresponding detection-element-side pad 121 via conductors formed respectively in a first through hole 105a provided in the first solid electrolyte body 105, a second through hole 107a provided in an insulation layer 107 described below, a fourth through hole 109a provided in a second solid electrolyte body 109, and a sixth through hole 111a provided in a protection layer 111. The end of the second lead portion 106b is electrically connected to a corresponding detection-element-side pad 121 via conductors formed respectively in a third through hole 107b provided in an insulation layer 107 described below, a fifth through hole 109b provided in the second solid electrolyte body 109, and a seventh through hole 111b provided in the protection layer 111.

Meanwhile, the oxygen pump cell 140 includes the second solid electrolyte body 109, and the third electrode 108 and a fourth electrode 110, which are formed on respective opposite sides of the second solid electrolyte body 109. The third electrode 108 includes a third electrode portion 108a and a third lead portion 108b extending from the third electrode portion 108a along the longitudinal direction of the second solid electrolyte body 109. The fourth electrode 110 includes a fourth electrode portion 110a and a fourth lead portion 110b extending from the fourth electrode portion 110a along the longitudinal direction of the second solid electrolyte body 109.

The end of the third lead portion 108b is electrically connected to a corresponding detection-element-side pad 121 via conductors formed respectively in the fifth through hole 109b provided in the second solid electrolyte body 109 and the seventh through hole 111b provided in the protection layer 111. Meanwhile, the end of the fourth lead portion 110b is electrically connected to a corresponding detection-element-side pad 121 via conductor formed in an eighth through hole 111c provided in the protection layer 111, described below. The second lead portion 106b and the third lead portion 108b have the same electric potential.

The first solid electrolyte body 105 and the second solid electrolyte body 109 are partially-stabilized-zirconia sintered bodies which are formed by adding yttria ($Y_2O_3$) or calcia (CaO) serving as a stabilizer to zirconia ($ZrO_2$).

The heat-generating element 102, the first electrode 104, the second electrode 106, the third electrode 108, the fourth electrode 110, the heater-side pads 120, and the detection-element-side pads 121 can be formed from a platinum group element. Platinum group elements which are preferred for forming these components include Pt, Rh and Pd. These elements can be used singly or in combination.

In order to provide heat resistance and resistance to oxidation, preferably, Pt is predominantly used to form the heat-generating element 102, the first electrode 104, the second electrode 106, the third electrode 108, the fourth electrode 110, the heater-side pads 120, and the detection-element-side pads 121. Furthermore, preferably, the heat-generating element 102, the first electrode 104, the second electrode 106, the third electrode 108, the fourth electrode 110, the heater-side pads 120, and the detection-element-side pads 121 contain a ceramic component in addition to a main component of a platinum group element(s). In order to promote attachment in a fixed condition, preferably, the ceramic component is similar to a material which is predominantly contained in a counterpart of the laminate (e.g., a main component of the first solid electrolyte body 105 and the second solid electrolyte body 109).

The insulation layer 107 is formed between the oxygen pump cell 140 and the oxygen concentration detection cell 130. The insulation layer 107 includes an insulation portion 114 and a diffusion resistor 115. The insulation portion 114 of the insulation layer 107 has a hollow measuring chamber 107c formed at a position corresponding to the second electrode portion 106a and the third electrode portion 108a. The measuring chamber 107c is in communication with the ambient atmosphere along the lateral direction of the insulation layer 107. In the communication region of the insulation layer 107, the diffusion resistor 115 is disposed so as to establish gas diffusion at a predetermined flow rate between the ambient atmosphere and the measuring chamber 107c.

No particular limitation is imposed on the insulation portion 114, so long as the insulation portion 114 is of an electrically insulative ceramic sintered body. Examples of such a ceramic sintered body include oxide ceramics, such as alumina and mullite.

The diffusion resistor 115 is made of a porous body of alumina. The diffusion resistor 115 controls the flow rate of a gas-to-be-measured when the gas flows into the measuring chamber 107c.

The protection layer 111 is formed on the surface of the second solid electrolyte body 109 such that the fourth electrode 110 is sandwiched therebetween. The protection layer 111 includes a porous electrode protection portion 113a, which covers the fourth electrode portion 110a for protecting the fourth electrode portion 110a from poisoning, and a reinforcement portion 112, which covers the second solid electrolyte body 109 for protecting the second solid electrolyte body 109, with the fourth lead portion 110b sandwiched therebetween. The gas sensor element 100 of the present embodiment corresponds to an oxygen sensor element which functions as follows: the direction and magnitude of current flowing between the electrodes of the oxygen pump cell 140 is adjusted such that voltage (electromotive force) generated between the electrodes of the oxygen concentration detection cell 130 has a predetermined value (e.g., 450 mV), and the oxygen concentration in a gas-to-be-measured is linearly detected according to current which flows in the oxygen pump cell 140.

Referring back to FIG. 1, the metallic shell 30 is made of SUS430 and includes an externally threaded portion 31 adapted to mount the gas sensor to an exhaust pipe, and a hexagonal portion 32 to which a mounting tool is fitted in mounting the gas sensor. The metallic shell 30 further includes a shell-side stepped portion 33, which projects radially inward. The shell-side stepped portion 33 supports a metal holder 34 for holding the gas sensor element 100. The metal holder 34 holds therein a ceramic holder 35 and a talc 36 disposed in this order in the rearward direction. The talc 36 is composed of a first talc 37 disposed within the metal holder 34, and a second talc 38 disposed in and outside the rear end of the metal holder 34. The first talc 37 is compressively charged into the metal holder 34, thereby fixing the gas sensor element 100 in relation to the metal holder 34. Also, the second talc 38 is compressively charged into the metallic shell 30, thereby ensuring a seal between the outer surface of the gas sensor element 100 and the inner surface of the metallic shell 30. A sleeve 39 made of alumina is disposed on the rear side of the second talc 38. The sleeve 39 is formed into a multi-stepped cylindrical shape and has an axial bore 39a extending along the axis. The gas sensor element 100 extends through the axial bore 39a. A rear-end crimp portion 30a of the metallic shell 30 is bent inward, thereby pressing the sleeve 39 toward the forward end of the metallic shell 30 via a ring member 40 made of stainless steel.

A protector 24 made of metal and having a plurality of gas intake holes 24a is welded to the outer circumferential surface of a forward end portion of the metallic shell 30 and covers a forward end portion of the gas sensor element 100 projecting from the forward end of the metallic shell 30. The protector 24 has a dual structure consisting of a closed-bottomed cylindrical outer protector 41 having a fixed outside diameter and a closed-bottomed cylindrical inner protector 42 disposed within the outer protector 41 and formed such that its rear end portion 42a is greater in outside diameter than its forward portion 42b.

Meanwhile, a forward end portion of a tubular sheath 25 made of SUS430 is fitted to a rear end portion of the metallic shell 30. The tubular sheath 25 is fixed to the metallic shell 30 by joining its diameter-expanded forward portion 25a to the metallic shell 30 by, for example, laser welding. A separator 50 is disposed within a rear portion of the tubular sheath 25. A holding member 51 intervenes between the separator 50 and the tubular sheath 25. The holding member 51 is engaged with a flange portion 50a of the separator 50 and is fixed between the tubular sheath 25 and the separator 50 by crimping the tubular sheath 25.

The separator 50 has a through hole 50b extending therethrough between its forward end and rear end for allowing insertion of lead wires 11 to 15 associated with the detection element 300 and the heater 200 (the lead wires 14 and 15 are not shown). The through hole 50b accommodates connection terminals 16 for connecting the lead wires 11 to 15 to the detection-element-side pads 121 of the detection element 300 and to the heater-side pads 120 of the heater 200. The lead wires 11 to 15 are connected to unillustrated external connectors. Electrical signals are transmitted between the lead wires 11 to 15 and external equipment, such as ECU, via the connectors. Although unillustrated in detail, the lead wires 11 to 15 have a structure in which a conductor is covered with an insulation film made of resin.

Furthermore, a substantially circular columnar rubber cap 52 is disposed on the rear side of the separator 50, for closing a rear end opening 25b of the tubular sheath 25. The rubber cap 52 fitted into the tubular sheath 25 is fixed to the tubular sheath 25 as follows: in a state in which the rubber cap 52 is fitted into the rear end of the tubular sheath 25, the tubular sheath 25 is crimped radially inward along its outer circumference. The rubber cap 52 also has through holes 52a extending therethrough between its forward end and rear end for allowing the lead wires 11 to 15 to extend through the respective through holes 52a.

Next described is a porous protection layer 20 (an inner porous layer 21 and an outer porous layer 23), which is a feature of the present invention.

FIG. 3 is a fragmentary, enlarged sectional view showing a forward end portion of the gas sensor element 100 shown in FIG. 1. As shown in FIG. 3, the inner porous layer 21 is provided directly on the surface of a laminate of the detection element 300 and the heater 200, and the outer porous layer 23 is formed so as to cover the outer surface of the inner porous layer 21. That is, the porous protection layer 20 is provided so as to entirely cover a forward end portion of the gas sensor element 100.

The expression "a forward end portion of the gas sensor element 100" refers to a portion of the gas sensor element 100 which extends along the direction of the axis L from the forward end of the gas sensor element 100 to an axial position corresponding to at least the rear end of the measuring chamber 107c. In the case of, for example, the $NO_x$ sensor element of FIG. 7, described below and which has a second measuring chamber 160 in communication with a measuring chamber 107c2, the forward end portion extends from the forward end of the gas sensor element 100 to the rear end of the second measuring chamber 160.

Figure 4:
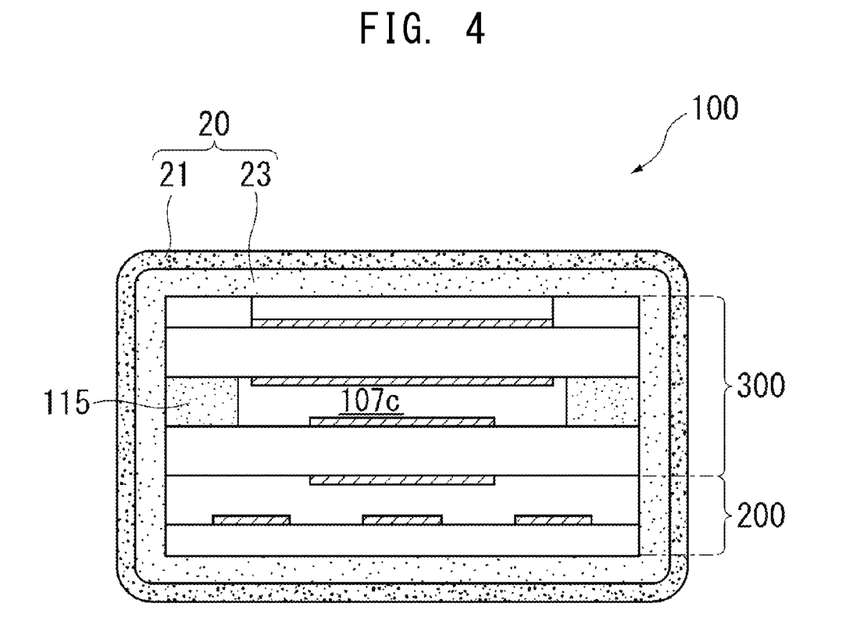
FIG. 4 is a schematic sectional view of a gas sensor element taken orthogonally to the direction of the axis.

The porous protection layer 20 is formed so as to cover the forward end surface of the gas sensor element 100 and extend rearward along the direction of the axis L while completely covering four surfaces; namely, the front and back surfaces and the opposite side surfaces, of the gas sensor element 100 (laminate) (see FIG. 4).

FIG. 4 is a schematic sectional view, taken orthogonally to the direction of the axis L, of the gas sensor element 100 including the inner porous layer 21 and the outer porous layer 23.

The inner porous layer 21 is adjacent to the outside of the diffusion resistor 115. The inner porous layer 21 porosity higher than that of the outer porous layer 23, and the inner porous layer 21 has a higher porosity than that of the diffusion resistor 115. In order to allow gas permeation, pores formed in the diffusion resistor 115, the inner porous layer 21, and the outer porous layer 23 are fashioned to have a three-dimensional network structure.

Generally, as the porosity of a porous layer increases, gas diffusion resistance tends to reduce as a result of an increase in pores in the porous layer. Thus, by providing the inner porous layer 21 having a porosity higher than that of the outer porous layer 23, the gas diffusion rate can be readily increased in the inner porous layer 21. The inner porous layer 21 is adjacent to the diffusion resistor 115 and has the narrowest gas penetration path (gas passage area) for introducing a gas from the ambient atmosphere. Furthermore, by means of the outer porous layer 23 having a porosity lower than that of the inner porous layer 21, the outer porous layer 23 having a reduced porosity effectively traps poisoning substances and water droplets. Thus, poisoning substances and water are unlikely to reach the detection element 300. Additionally, by means of the inner porous layer 21 having a porosity higher than that of the outer porous layer 23, the total volume of voids (empty spaces) contained in the inner porous layer 21 increases, thereby imparting thermal insulation properties to the inner porous layer 21. Therefore, even when the outer porous layer 23 is cooled by adhesion of water, the detection element 300 is unlikely to be suddenly cooled. Even in a state in which the heater 200 heats the detection element 300, damage to the gas sensor element 100 caused by adhesion of water can be effectively restrained.

Also, by means of the inner porous layer 21 having porosity higher than that of the diffusion resistor 115, the gas introduced from the ambient atmosphere readily flows through the inner porous layer 21 toward the diffusion resistor 115.

As mentioned above with reference to FIG. 10, the gas diffusion resistance of a porous layer depends greatly on not only porosity but also pore diameter. Thus, as shown in FIG. 5, in the present invention, as viewed in a plurality of 100 µm×100 µm regions $a_1$ to $a_3$ and $b_1$ to $b_3$ on a scanning electron micrograph of the sections of the inner porous layer and the diffusion resistor 115, a pore diameter ($C_{IN}$ FIG. 5) greater than the greatest pore diameter $C_{DIF}$ in the regions $b_1$ to $b_3$ of the diffusion resistor 115 exists in each of the regions $a_1$ to $a_3$ of the inner porous layer 21.

Figure 5:
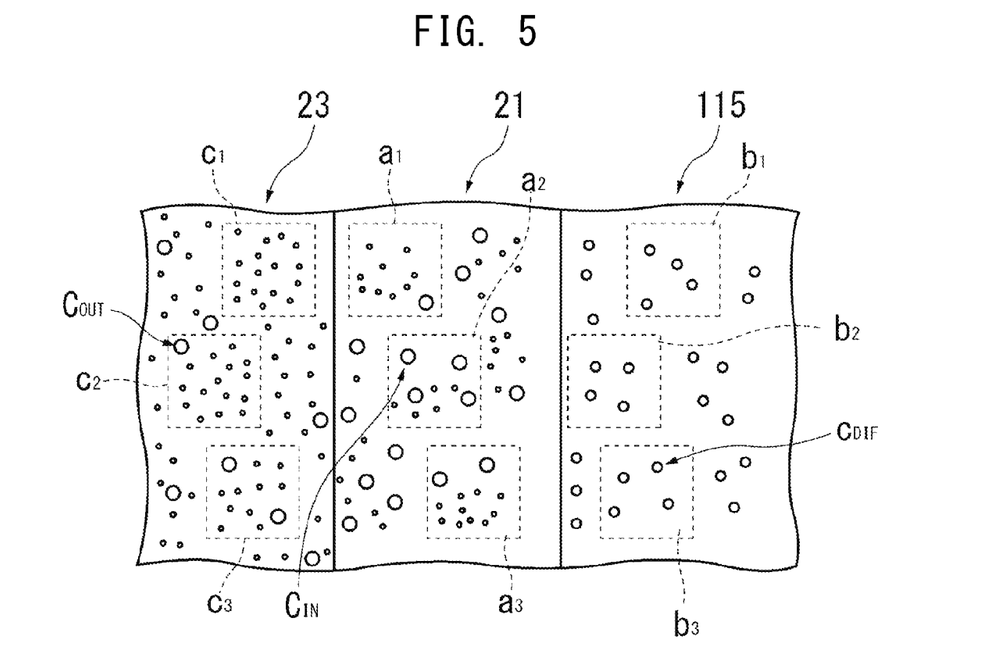
FIG. 5 is a schematic view showing a plurality of 100 µm×100 µm regions on a scanning electron micrograph of the sections of a diffusion resistor, an inner porous layer, and an outer porous layer.

For example, in the example of FIG. 5, the greatest pore diameter selected from diameters of pores contained in the region $b_3$ is greater than the greatest pore diameter selected from diameters of pores contained in the regions $b_1$ and $b_2$ and is denoted by $C_{DIF}$. Each of the regions $a_1$ to $a_3$ is checked to determine whether or not a pore diameter $C_{IN}$ greater than the greatest pore diameter $C_{DIF}$ of the diffusion resistor 115 exists therein. FIG. 5 shows a section taken perpendicularly to the vertical direction on the paper on which FIG. 3 appears (i.e., a section taken perpendicularly to the laminating direction). As viewed on this section, a plurality of 100 µm×100 µm regions are observed on the scanning electron micrograph of the diffusion resistor 115 and the inner porous layer 21. If, in this section the 100 µm×100 µm regions are not available, examination may be made on a section which is taken along another direction and in which the 100 µm×100 µm regions are available.

By means of the pore diameter $C_{IN}$ greater than the greatest pore diameter $C_{DIF}$ in the diffusion resistor 115 existing in each of the regions $a_1$ to $a_3$ of the inner porous layer 21, large-diameter pores (the pores shown in FIG. 9A which allow molecular diffusion faster than fine-pore diffusion) reliably exist in the inner porous layer 21. Accordingly, the gas diffusion resistance of the inner porous layer 21 is reliably reduced, thereby facilitating diffusion (introduction) of gas into the measuring chamber 107c. Thus, deterioration in sensor output can be restrained.

Notably, all of pores in the inner porous layer 21 are not necessarily greater in diameter than pores in the diffusion resistor 115. For example, as shown in FIG. 5, pore diameters smaller than $C_{DIF}$ may exist in the inner porous layer 21. However, as mentioned above with reference to FIG. 10, by means of large-diameter pores (pores which allow molecular diffusion) reliably existing in the above-mentioned regions $a_1$ to $a_3$, the regions collectively serve as a path which allow molecular diffusion, thereby reducing gas diffusion resistance.

As shown in FIG. 5, one or more pores having a pore diameter $C_{OUT}$ greater than the greatest pore diameter $C_{DIF}$ in the diffusion resistor 115 exist in some of a plurality of 100 μm×100 μm regions $c_1$ to $c_3$ on a scanning electron micrograph of the section of the outer porous layer 23. By virtue of this feature, gas can sufficiently pass through the outer porous layer 23. However, preferably, in view of effective trapping of poisoning substances and water droplets in the outer porous layer, the pore diameter $C_{OUT}$ greater than the greatest pore diameter $C_{DIF}$ in the diffusion resistor 115 does not exist in some of the plurality of 100 μm×100 μm regions $c_1$ to $c_3$ in the outer porous layer 23. For example, in the example of FIG. 5, one pore having the pore diameter $C_{OUT}$ exists in the region $c_2$, and two pores having the pore diameter $C_{OUT}$ exist in the region $c_3$. However, a pore having the pore diameter $C_{OUT}$ does not exist in the region $c_1$. Although the diffusion resistance of the outer porous layer 23 is relatively high, since the gas penetration path expands with an outward distance from the diffusion resistor 115, gas can pass through the outer porous layer 23.

The inner porous layer 21 is formed, for example, by joining together, by firing or the like, particles of ceramic selected singly or in combination from the group consisting of alumina, spinel, zirconia, mullite, zircon and cordierite. By sintering a slurry which contains the particles, pores can be formed in the framework of a film. However, preferably, a slurry which contains the particles and a burning-off-type pore-forming material is sintered. The pore-forming material burns off to become pores, whereby the inner porous layer 21 can have high porosity as mentioned below. Examples of a usable pore-forming materials include carbon, resin beads, and organic or inorganic binder particles.

Preferably, the porosity of the inner porous layer 21 obtained by image analysis, described below, is 50% to 75%, since the above-mentioned effect can be readily obtained. When the porosity of the inner porous layer 21 is 50% or less, the gas diffusion resistance of the inner porous layer 21 tends to increase. A film having a porosity in excess of 75% may be difficult to manufacture.

Preferably, the inner porous layer 21 has a thickness of 20 μm to 800 μm.

The outer porous layer 23 is formed, for example, by joining together, by firing or the like, particles of ceramic selected singly or in combination from the group consisting of alumina, spinel, zirconia, mullite, zircon and cordierite. By sintering a slurry which contains the particles, pores are formed in the framework of a film. The pores are formed in gaps among ceramic particles and as a result of burning off of organic or inorganic binder contained in the slurry.

Preferably, the porosity of the outer porous layer 23 obtained by image analysis, described below, is 30% to 50%, since a barrier to poisoning substances and water droplets is ensured without deterioration in gas permeability. When the porosity of the outer porous layer 23 is less than 30%, poisoning substances are apt to cause clogging. When the porosity of the outer porous layer 23 is in excess of 50%, water may penetrate into the outer porous layer 23, potentially resulting in deterioration in resistance to adhesion of water.

Preferably, the outer porous layer 23 has a thickness of 100 μm to 800 μm.

The diffusion resistor 115 can also be formed, for example, by joining together, by firing or the like, particles of ceramic selected singly or in combination from the group consisting of alumina and zirconia. By sintering a slurry which contains the particles, pores are formed in the framework of a film. The pores are formed in gaps among ceramic particles and as a result of burning off of organic or inorganic binder contained in the slurry. As in a publicly known manufacturing method, the diffusion resistor 115 is formed as follows: before the gas sensor element 100 (the detection element 300) is formed by firing, a green body of the diffusion resistor 115 and green component layers are laminated together, and the resultant green laminate is fired.

Preferably, the porosity of the diffusion resistor 115 obtained by image analysis is 40% to 55%. By employing such a porosity, gas permeability does not deteriorate and thus, sensor output is not reduced. When the porosity of the diffusion resistor 115 is less than 40%, gas permeability deteriorates, resulting in a reduction in sensor output. When the porosity of the diffusion resistor 115 is in excess of 55%, difficulty is encountered in controlling the gas diffusion rate, potentially resulting in a failure to generate limiting current.

Preferably, the diffusion resistor 115 has a thickness of 10 μm to 50 μm.

The porosities of the diffusion resistor 115, the inner porous layer 21, and the outer porous layer 23 are obtained as follows.

First, a micrograph (SEM image) of the sections of the diffusion resistor 115, the inner porous layer 21, and the outer porous layer 23 is binarized at a plurality of positions on each of the micrographed sections by use of commercially available image analysis software. The percentage of black portions on each of the micrographed sections is obtained. Black portions on the micrographed sections correspond to pores, and white portions correspond to the framework of a film. Thus, the greater the occupancy of black portions, the higher the porosity.

Porosities obtained by image analysis conducted at the plurality of positions on each of the micrographed sections of the diffusion resistor 115, the inner porous layer 21, and the outer porous layer 23 are averaged, to thereby obtain the porosity of each of the layers.

The above-mentioned greatest pore diameter $C_{DIF}$ and pore diameters $C_{IN}$ and $C_{OUT}$ are measured as follows: a plurality of 100 μm×100 μm regions are determined on each of the micrographed sections (the sections appearing on the SEM image); the regions are binarized by use of the commercially available image analysis software; and the diameters of black portions in the regions are obtained. The diameter of a black portion is the diameter of a circle to which a black portion is approximated.

In the first embodiment, both of the inner porous layer 21 and the outer porous layer 23 entirely cover a forward end portion of the laminate. Since the inner porous layer 21 is higher in porosity than the outer porous layer 23, by means of the inner porous layer 21 entirely covering a forward end portion of the laminate of the detection element 300 and the heater 200, the total volume of voids in the inner porous layer 21, which is located on a side toward the laminate, further increases, thereby further enhancing thermal insulation performance. Therefore, even when the outer porous layer 23 is cooled by adhesion of water, the gas sensor element 100 is unlikely to be suddenly cooled. Therefore, even in a state in which the heater 200 heats the detection element 300, damage to the gas sensor element 100 caused by adhesion of water can be more effectively restrained.

Incidentally, another porous layer may be provided between the inner porous layer 21 and the outer porous layer 23. Also, another porous layer may be provided externally of the outer porous layer 23.

The inner porous layer 21 and the outer porous layer 23 may be formed by the following method: slurries which will become the inner porous layer 21 and the outer porous layer 23 are sequentially applied by, for example, a dipping process, followed by sintering. In this case, after the slurry which will become the inner porous layer 21 is applied and sintered, the slurry which will become the outer porous layer 23 may be applied and sintered. Alternatively, the slurries which will become the inner porous layer 21 and the outer porous layer 23 are sequentially applied, followed by batch sintering.

Also, a thermal spraying process, a printing process, or a spraying process may be used to form the inner porous layer 21 and the outer porous layer 23. Furthermore, the inner porous layer 21 and the outer porous layer 23 may be formed by respectively different processes selected from among the dipping process, the thermal spraying process, the printing process, and the spraying process.

Figure 6:
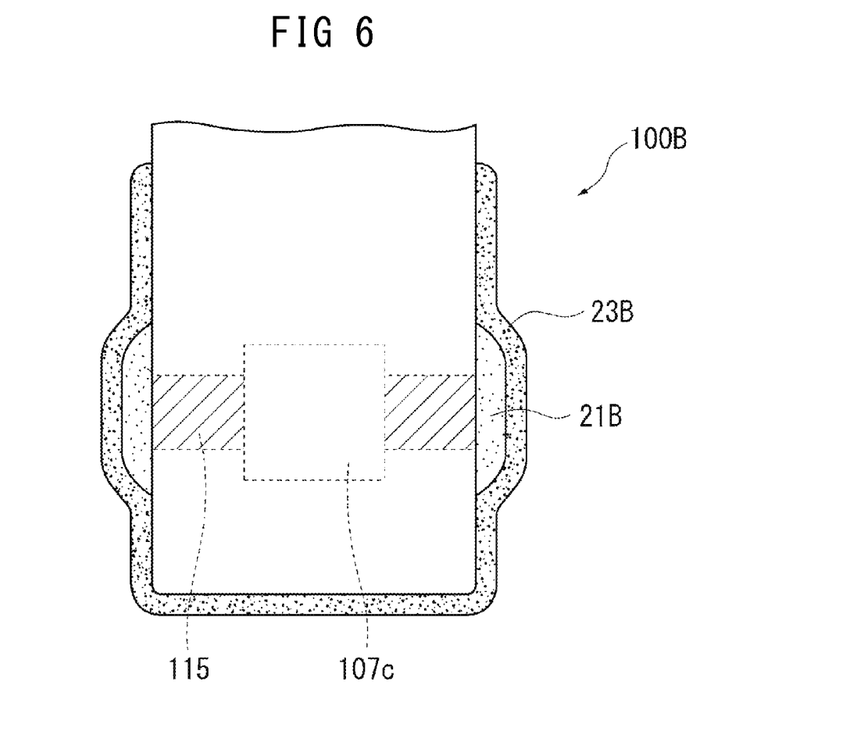
FIG. 6 is a sectional view showing a modification of the gas sensor element of the first embodiment, taken along the longitudinal direction of the gas sensor element.

FIG. 6 shows a modification of the gas sensor element 100 of the first embodiment. In a gas sensor element 100B of FIG. 6, since a detection element and a heater are similar to those (the oxygen sensor element in FIG. 2) of the first embodiment, description thereof is omitted.

In the gas sensor element 100B, an inner porous layer 21B does not entirely cover a forward end portion of the laminate, but covers only the diffusion resistor 115 and its periphery. By contrast, an outer porous layer 23B entirely covers the forward end portion of the laminate. The example of FIG. 6 also has the following features: the inner porous layer 21B is higher in porosity than the outer porous layer 23B; the inner porous layer 21B is higher in porosity than the diffusion resistor 115; and a pore diameter $C_{IN}$ greater than the greatest pore diameter $C_{DIF}$ in the diffusion resistor 115 exists in each of a plurality of regions in the inner porous layer 21B. Thus, similar to the first embodiment, large-diameter pores (pores shown in FIG. 9A which allow molecular diffusion) reliably exist in the inner porous layer 21B. Accordingly, the gas diffusion resistance of the inner porous layer 21B is reliably reduced, thereby facilitating diffusion (introduction) of gas into the measuring chamber 107c. Thus, deterioration in sensor output can be restrained.

Next, a gas sensor ($NO_x$ sensor) according to a second embodiment of the present invention will be described with reference to FIG. 7. The gas sensor according to the second embodiment is similar to the gas sensor according to the first embodiment except for the configurations of a gas sensor element 100C, an inner porous layer 21C, and an outer porous layer 23C. Thus, the description and illustration of the metallic shell for holding the gas sensor element 100C, and like components are omitted.

Since the $NO_x$ sensor has a lower sensor output as compared with an oxygen sensor, deterioration in sensor output is more susceptible to obstruction in diffusion (introduction) of gas into the measuring chamber as compared with the oxygen sensor. Thus, the present invention is more effectively applied to an $NO_x$ sensor by providing the inner porous layer 21C and the outer porous layer 23C on the surface of the laminate of the $NO_x$ sensor element as in the case of the second embodiment.

The gas sensor element ($NO_x$ sensor element) 100C has a narrow, elongated plate shape and a structure in which three plate-like solid electrolyte bodies 109C, 105C and 151 are arranged in layers while insulators 180 and 185 made of, for example, alumina are individually sandwiched therebetween. The laminate structure serves as a detection element 300C. A heater 200C is provided on the outer side (opposite the solid electrolyte layer 105C in FIG. 7) of the solid electrolyte body 151. The heater 200C is configured such that a heater pattern 102C formed predominantly from Pt is sandwiched between sheet-like insulation layers 103C and 101C formed predominantly from alumina.

The solid electrolyte bodies 109C, 105C and 151 are formed from zirconia, which is a solid electrolyte having oxygen ion conductivity.

The detection element 300C includes a first pump cell (Ip1 cell) 140C, an oxygen-concentration detection cell (Vs cell) 130C, and a second pump cell (Ip2 cell) 150, which are described below. The first pump cell 140C and the oxygen-concentration detection cell 130C correspond to the "cell" of the invention.

The first pump cell 140C includes the second solid electrolyte body 109C, and a third electrode 108C and a fourth electrode 110C formed respectively on the opposite surfaces of the second solid electrolyte body 109C. A porous protection layer 114 formed from ceramic is provided on the surface of the fourth electrode 110C for protecting the fourth electrode 110C against deterioration caused by exposure to a poisoning gas (a reducing atmosphere) contained in exhaust gas.

The first pump cell 140C functions similarly to the oxygen pump cell 140 in that the first pump cell 140C pumps oxygen (so-called oxygen pumping) between the ambient atmosphere and a first measuring chamber 107c2, described below, via the second solid electrolyte body 109C.

The oxygen-concentration detection cell 130C includes the first solid electrolyte body 105C and a first electrode 104C and a second electrode 106C formed respectively on the opposite surfaces of the first solid electrolyte body 105C. The oxygen-concentration detection cell 130C can generate an electromotive force according to the difference in partial pressure of oxygen between the first measuring chamber 107c2 and a reference oxygen chamber 170, which are separated from each other by the first solid electrolyte body 105C, the reference oxygen chamber 170 described below.

The first measuring chamber 107c2, which is a small hollow space, is formed between the second solid electrolyte body 109C and the first solid electrolyte body 105C. The second electrode 106C and the third electrode 108C are disposed within the first measuring chamber 107c2. The first measuring chamber 107c2 is a small space of the gas sensor element 100C into which a gas-to-be-measured from the ambient atmosphere is first introduced, and corresponds to the "measuring chamber" of the invention.

A porous first diffusion resistor 115C is disposed in the first measuring chamber 107c2 on a side toward the forward end of the gas sensor element 100C. The first diffusion resistor 115C intervenes between the first measuring chamber 107c2 and the ambient atmosphere and is adapted to adjust diffusion of the gas-to-be-measured into the first measuring chamber 107c2. The first diffusion resistor 115C corresponds to the "diffusion resistor" of the invention.

Furthermore, a second diffusion resistor 117 is disposed in the first measuring chamber 107c on a side toward the rear end of the gas sensor element 100C. The second diffusion resistor 117 serves as a partition between the first measuring chamber 107c2 and an opening portion 181 connected to the second measuring chamber 160, described below, and is adapted to adjust diffusion of gas. Since the gas-to-be-measured from the ambient atmosphere is not introduced directly into the second measuring chamber 160, the second measuring chamber 160 does not correspond to the "measuring chamber" of the invention. Also, since the second diffusion resistor 117 does not intervene between the first measuring chamber 107c2 and the ambient atmosphere, the second diffusion resistor 117 does not correspond to the "diffusion resistor" of the invention.

Meanwhile, each of the second electrode 106C and the third electrode 108C corresponds to "one of the pair of electrodes" of the invention.

Furthermore, the gas sensor element 100C includes a second pump cell 150 composed of the third solid electrolyte body 151, a fifth electrode 152, and a sixth electrode 153. The third solid electrolyte body 151 is disposed so as to face the first solid electrolyte body 105C with the insulator 185 sandwiched therebetween. The insulator 185 is not disposed at the position where the fifth electrode 152 is formed, thereby forming the reference oxygen chamber 170 in the form of an independent space. The first electrode 104C of the oxygen-concentration detection cell 130C is also disposed in the reference oxygen chamber 170. The reference oxygen chamber 170 is filled with a porous body made of ceramic. Also, the insulator 185 is not disposed at a position where the sixth electrode 153 is formed, thereby forming the hollow second measuring chamber 160 in the form of an independent space. In this manner, the insulator 185 separates the reference oxygen chamber 170 and the second measuring chamber 160 from each other. The first solid electrolyte body 105C and the insulator 180 have opening portions 125 and 181, respectively, formed so as to communicate with the second measuring chamber 160. Thus, as mentioned above, the first measuring chamber 107c2 and the opening portion 181 are connected to each other with the second diffusion resistor 117 intervening therebetween.

The second pump cell 150 can pump oxygen between the reference oxygen chamber 170 and the second measuring chamber 160, which are separated from each other by the insulator 185.

Since the fifth electrode 152 and the sixth electrode 153 of the second oxygen pump cell 150 do not face the first measuring chamber 107c2, the second oxygen pump cell 150 does not correspond to the "cell" of the invention.

The inner porous layer 21C is provided directly on the surface of a laminate of the detection element 300C and the heater 200C, and the outer porous layer 23C is formed so as to cover the outer surface of the inner porous layer 21C. That is, a porous protection layer 20C (the inner porous layer 21C and the outer porous layer 23C) is provided so as to entirely cover a forward end portion of the gas sensor element 100C.

In the case of the gas sensor element 100C, which is an NOx sensor element, since another measuring chamber (the second measuring chamber 160) communicates with the first measuring chamber 107c2 at the rear end of the first measuring chamber 107c2, the porous protection layer 20C extends rearward beyond the rear end of the second measuring chamber 160.

Similar to the first embodiment, the porous protection layer 20C completely covers four surfaces; namely, the front and back surfaces and the opposite side surfaces, of the gas sensor element 100C (laminate).

Also, in the second embodiment, the inner porous layer 21C has a higher porosity than the outer porous layer 23C; the inner porous layer 21C has a higher porosity than the diffusion resistor 115C; and a pore diameter $C_{IN}$ greater than the greatest pore diameter $C_{DIF}$ in the diffusion resistor 115C exists in each of a plurality of regions in the inner porous layer 21C. Thus, similar to the first embodiment, large-diameter pores (pores shown in FIG. 9A which allow molecular diffusion) reliably exist in the inner porous layer 21C. Accordingly, the gas diffusion resistance of the inner porous layer 21C is reliably reduced, thereby facilitating diffusion (introduction) of gas into the first measuring chamber 107c2. Thus, deterioration in sensor output can be restrained.

Furthermore, in the case of the gas sensor element 100C, since the inner porous layer 21C and the outer porous layer 23C entirely cover a forward end portion of the laminate, and the inner porous layer 21C is higher in porosity than the outer porous layer 23C, the thermal insulation performance of the gas sensor element 100C is enhanced. Therefore, even when the outer porous layer 23C is cooled by adhesion of water, the gas sensor element 100C is unlikely to be suddenly cooled. Therefore, even in a state in which the heater 200C heats the detection element 300C, damage to the gas sensor element 100C caused by adhesion of water can be more effectively restrained.

Next, operation of the $NO_x$ sensor element 100C for detecting $NO_x$ concentration will be briefly described. First, the first pump cell 140C pumps oxygen out of the first measuring chamber 107c2 to the ambient atmosphere or pumps oxygen into the first measuring chamber 107c2 from the ambient atmosphere so as to maintain the potential difference between the electrodes 104C and 106C at a fixed level near 425 mV.

Exhaust gas whose oxygen concentration is adjusted in the first measuring chamber 107c2 as mentioned above is introduced into the second measuring chamber 160 via the second diffusion resistor 117. $NO_x$ contained in the exhaust gas comes into contact with the sixth electrode 153 in the second measuring chamber 160 and is decomposed (reduced) into $N_2$ and $O_2$ by the catalytic effect of the sixth electrode 153. Oxygen generated through decomposition receives electrons from the sixth electrode 153 and becomes oxygen ions. The oxygen ions flow through the third solid electrolyte layer 151 to the fifth electrode 152. At this time, residual oxygen which is left unpumped in the first measurement chamber 107c2 similarly moves into the reference oxygen chamber 170 through the Ip2 cell 150. Thus, current flowing through the Ip2 cell 150 consists of current stemming from $NO_x$ and current stemming from the residual oxygen.

Since the residual oxygen which is left unpumped in the first measurement chamber 107c2 is adjusted to a predetermined concentration as mentioned above, current stemming from the residual oxygen can be considered substantially constant. Thus, its effect on variation in current stemming from $NO_x$ is small. Therefore, current flowing through the Ip2 cell 150 is proportional to $NO_x$ concentration.

The present invention is not limited to the above-described embodiments, but is applicable to any gas sensor (gas sensor element) which has a heater, and a detection element having a solid electrolyte body and a pair of electrodes. The present invention is applied to an oxygen sensor (oxygen sensor element) and an $NO_x$ sensor ($NO_x$ sensor element) in the above-described embodiments, but application of the present invention is not limited thereto. Needless to say, the present invention may encompass various modifications and equivalents thereof without departing from the spirit and scope of the invention. For example, the present invention may be applied to an HC sensor (HC sensor element) for detecting HC concentration.

EXAMPLES

A gas sensor element of Example 1 is described as follows.

A slurry A for forming the inner porous layer 21C was prepared as described below and adjusted so as to have an appropriate viscosity. The slurry A was applied, by a dipping process, to the surfaces (front and back surfaces and opposite side surfaces) of forward end portions of the plate-like gas sensor elements ($NO_x$ sensor elements) 100C shown in FIG. 7 in such a manner as to have a thickness of 200 μm. Subsequently, in order to volatilize excess organic solvent contained in the applied slurry A, the gas sensor elements 100C were dried for several hours by a drier which was set at 200° C., followed by firing at 1,100° C. in the atmosphere for three hours for forming the inner porous layers 21C.

The slurry A was prepared as follows: 40 vol. % alumina powder (average particle size: 0.1 μm), 60 vol. % carbon powder (average particle size: 20.0 μm), and 10 wt. % alumina sol were measured out and mixed; an organic solvent was added to the mixture; and the resultant mixture was stirred. The average particle size was obtained by a laser diffraction scattering method.

A slurry B for forming the outer porous layer 23C was prepared as described below and adjusted so as to have an appropriate viscosity. The slurry B was applied, by a dipping process, to the surfaces of the inner porous layers 21C such that the applied slurry B had various thicknesses of 150 μm or more (see FIG. 8). Subsequently, in order to volatilize excess organic solvent contained in the applied slurry B, the gas sensor elements 100C were dried for several hours by the drier which was set at 200° C., followed by firing at 1,100° C. in the atmosphere for three hours for forming the outer porous layers 23C.

The slurry B was prepared as follows: 20 vol. % alumina powder (average particle size: 0.1 μm), 80 vol. % spinel powder (average particle size: 40.0 μm), and 10 wt. % alumina sol were measured out and mixed; an organic solvent was added to the mixture; and the resultant mixture was stirred.

A slurry used to form the diffusion resistor 115C was prepared as follows: 100 mass % alumina powder and a plasticizer were wet-mixed for dispersion of the alumina powder. The plasticizer was composed of butyral resin and DBP. Similar to a publicly known manufacturing method, by use of the slurry, before the gas sensor elements 100C were formed by firing, green bodies of the diffusion resistor 115C and green component layers were laminated together, and the resultant laminates were fired.

The thus-obtained gas sensor elements 100C each including the diffusion resistor 115C, the inner porous layer 21C, and the outer porous layer 23C were sectioned along a direction orthogonal to the direction of lamination. The sections were image-captured using a scanning electron micrograph (SEM), thereby obtaining micrographed sections.

On the obtained micrographed sections, the diffusion resistor 115C, the inner porous layer 21C, and the outer porous layer 23C were image-analyzed to obtain the percentage of black portions. In image analysis of each of the diffusion resistor 115C, the inner porous layer 21C, and the outer porous layer 23C, porosity was obtained for four 100 μm×100 μm regions; the obtained porosities of the four regions were averaged; and the average porosity was taken as the porosity of each of the layers. The inner porous layer 21C was checked to determine whether a pore diameter $C_{IN}$ greater than the greatest pore diameter $C_{DIF}$ in the diffusion resistor 115C exists in each of the regions thereof. As mentioned above, the greatest pore diameter $C_{DIF}$ in the diffusion resistor 115C is the greatest pore diameter out of diameters of pores contained in the four regions.

In this manner, the porosity (average porosity) was determined for each of the diffusion resistor 115C, the inner porous layer 21C and the outer porous layer 23C, and whether or not the pore diameter $C_{IN}$ exists was also determined.

Notably, Example 1 refers to the gas sensor elements in which the inner porous layer 21C and the outer porous layer 23C are formed so as to entirely cover a forward end portion of the laminate. Example 2 relates to the gas sensor elements in which the inner porous layer 21C is formed so as to cover only the diffusion resistor 115C and its periphery (equivalent to FIG. 6).

Figure 7:
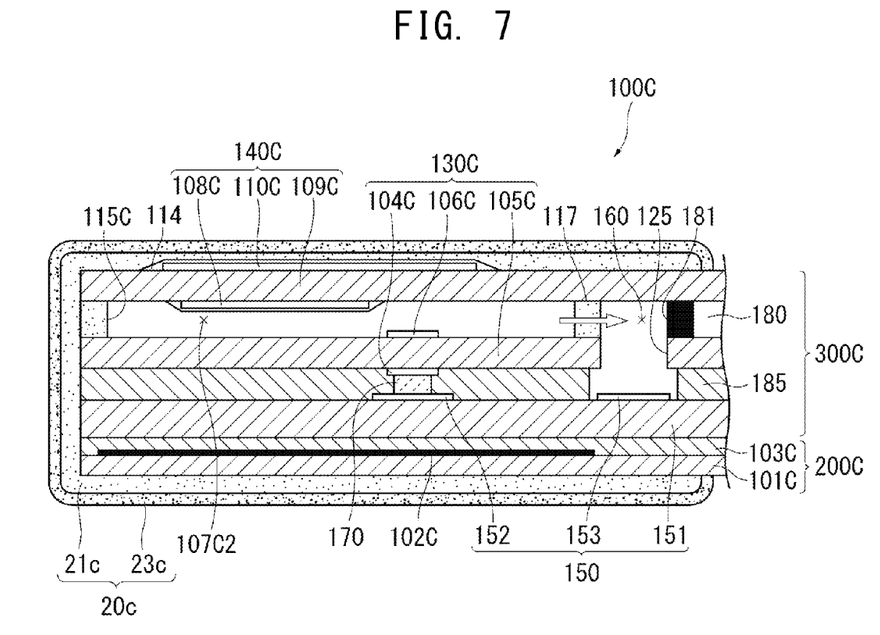
FIG. 7 is a sectional view of a gas sensor element, taken along the longitudinal direction of the gas sensor element, in a gas sensor (NOx sensor) according to a second embodiment of the present invention.

$NO_x$ sensor elements of Comparative Example 1 were manufactured in a manner similar to that for manufacturing the gas sensor elements of Example 1 above except that, by use of the slurry B only, a single porous detection layer was formed, by firing, on the surface (front and back surfaces and opposite side surfaces) of a forward end portion of the plate-like gas sensor element ($NO_x$ sensor element) 100C shown in FIG. 7.

Similar to Example 1, the thus-obtained gas sensor elements of Example 2 and Comparative Example 1 were sectioned along a direction orthogonal to the laminating direction. The sections were image-captured through the scanning electron micrograph (SEM), to thereby obtain micrographed sections. On the basis of the micrographed sections, the porosity (average porosity) was determined for the diffusion resistor 115C, the inner porous layer 21C, and the outer porous layer 23C (in the case of Comparative Example 1, the porosity of the porous protection layer was determined), and whether or not the pore diameter $C_{IN}$ exists was determined.

By use of the gas sensor elements of Examples 1 and 2 and Comparative Example 1 in which the porous protection layer was formed as described above, gas sensors ($NO_x$ sensors) were manufactured. In a state in which the sensor element temperature was held at 700° C., the sensor output of gas sensors was measured.

A gas sensor element was prepared in which the porous protection layer was not formed such that the diffusion resistor 115C was in direct contact with the ambient atmosphere. By use of the gas sensor element, a gas sensor was manufactured. The sensor output of the gas sensor was similarly measured. The obtained sensor output was used as a base sensor output. The variation rate of sensor output was obtained by the following expression.

(Sensor output variation rate)={(sensor output)−(base sensor output)}/(base sensor output)×100

The sensor output variation rate indicates the following: the closer to zero the sensor output variation rate, the lower the gas diffusion resistance of the inner porous layer 21C in contact with the diffusion resistor 115C. Namely, a greater degree of diffusion (introduction) of gas into the measuring chamber 107c results in reduced deterioration in sensor output.

Figure 8:
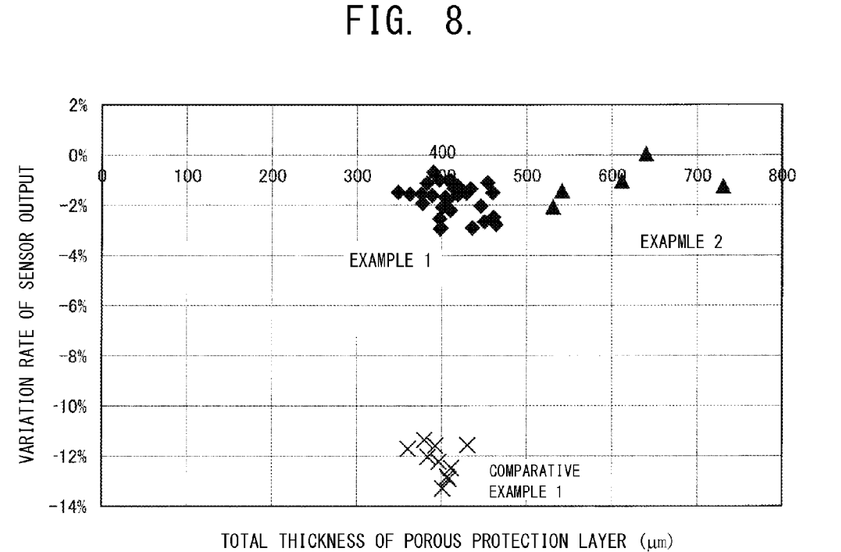
FIG. 8 is a graph showing sensor output variation rates of Examples 1 and 2 and Comparative Example 1.

The measurement results are shown in Table 1 and FIG. 8.

visually check if the outer surface of the porous protection layer was damaged. Furthermore, the porous protection layer was peeled away. Then, the gas sensor element was visually

TABLE 1

| | Porosity (%) | | | | | Sensor output variation rate (%) |
|---|---|---|---|---|---|---|
| | Diffusion resistor | Inner porous layer | Outer porous layer | Region of formation of inner porous layer | Existence of porosity $C_{IN}$ in four regions (Y: Yes; N: No) | |
| Example 1 | 45 | 69 | 38 | Entire forward end portion of laminate | Region 1: Y; Region 2: Y; Region 3: Y; Region 4: Y | −1.8 |
| Example 2 | 45 | 69 | 38 | Diffusion resistor and its periphery | Region 1: Y; Region 2: Y; Region 3: Y; Region 4: Y | −1.1 |
| Comparative Example 1 | 45 | 38 | — | | Region 1: Y; Region 2: N; Region 3: N; Region 4: N | −12.2 |

As is apparent from Table 1 and FIG. 8, in the case of Examples 1 and 2 (in which the inner porous layer 21C and the outer porous layer 23C were provided, the inner porous layer 21C had a higher porosity than the outer porous layer 23C; the inner porous layer 21C had a higher porosity than the diffusion resistor 115C; and a pore diameter $C_{IN}$ greater than the greatest pore diameter $C_{DIF}$ in the diffusion resistor 115C existed in each of a plurality of regions in the inner porous layer 21C), the sensor output variation rate assumed a small value of −1.8% (average) and −1.1% (average), respectively.

By use of the gas sensor elements which were similar in configuration to Example 1 and having an inner porous layer 21C thickness ranging from 20 μm to 270 μm while the total thickness of the inner porous layer 21C and the outer porous layer 23C was 400 μm, the variation of sensor output was measured in a similar manner. The results of measurement were equivalent to those of Example 1.

By contrast, in the case of Comparative Example 1, in which a single porous protection layer was formed, and the pore diameter $C_{IN}$ greater than the greatest pore diameter $C_{DIF}$ in the diffusion resistor 115C existed only in some of a plurality of regions in the porous protection layer (equivalent of the inner porous layer 21C), the of sensor output variation rate assumed a large value of −12.2% (average).

Next, a water adhesion test was conducted using the gas sensor elements of Example 1 and Comparative Example 2.

The $NO_x$ sensor elements of Comparative Example 2 were manufactured in a manner similar to that of Example 1, except that the inner porous layer was formed using the slurry B so as to entirely cover a forward end portion of the laminate and the outer porous layer was formed on the inner porous layer using the slurry A.

First, in the atmosphere, a water droplet of 3 μL and a water droplet of 10 μL were dropped 20 times each on the porous protection layer at a position corresponding to the diffusion resistor 115C while the sensor element was held at a temperature of 800° C. Subsequently, by use of a magnifier, the appearance of the porous protection layer was observed to visually check if the outer surface of the porous protection layer was damaged. Furthermore, the porous protection layer was peeled away. Then, the gas sensor element was visually checked for the generation of cracks by a red check method well known to those of ordinary skill in this field of art (a flaw detection method which applies a red penetrant to the element surface). Ten pieces each of Example 1 and Comparative Example 2 were examined to evaluate damage to the porous protection layer and cracking in the gas sensor element, and the number of gas sensor elements which suffered damage and cracking was counted.

Table 2 shows the inspection results.

TABLE 2

| | Porosity (%) | | | Water adhesion test (3 μL) | | Water adhesion test (10 μL) | |
|---|---|---|---|---|---|---|---|
| | Diffusion resistor | Inner porous layer | Outer porous layer | Damage to porous protection layer | Cracking in gas sensor element | Damage to porous protection layer | Cracking in gas sensor element |
| Example 1 | 45 | 69 | 38 | 0 | 0 | 0 | 0 |
| Comparative Example 2 | 45 | 38 | 69 | 4 | 7 | 10 | 10 |

As is apparent from Table 2, in the case of subjecting Example 1 (in which the inner porous layer 21C was provided so as to entirely cover a forward end portion of the laminate, and the outer porous layer 23C was provided on the surface of the inner porous layer 21C) to the water adhesion test, the porous protection layers were found to be free from damage, and the gas sensor elements 100C were free from cracking, indicating that resistance to adhesion of water was excellent.

By contrast, in the case of subjecting Comparative Example 2 (in which the inner porous layer had a lower porosity than the outer porous layer) to the water adhesion test, the porous protection layers were found to have been damaged, and the gas sensor elements were cracked, indicating that resistance to water adhesion was poor.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2011-238736 filed Oct. 31, 2011, incorporated herein by reference in its entirety.

What is claimed is:

1. A gas sensor element comprising:
a laminate of a detection element and a heater; and
a porous protection layer which entirely covers a forward end portion of the laminate, wherein the detection element has at least one cell composed of a solid electrolyte body and a pair of electrodes disposed on the solid electrolyte body;

the heater has an insulating ceramic body and a heat-generating element provided in the insulating ceramic body and adapted to generate heat by passing electric current therethrough; and the laminate has at least one measuring chamber which is formed in its forward end portion, into which a gas-to-be-measured is introduced from an ambient atmosphere via a diffusion resistor, and which one of the pair of electrodes faces, the gas sensor element being characterized in that the porous protection layer comprises an inner porous layer disposed externally of the diffusion resistor and covering at least the diffusion resistor, and an outer porous layer formed externally of the inner porous layer and entirely covering the forward end portion of the laminate;

the inner porous layer has a higher porosity than the outer porous layer;

the porosity of the inner porous layer is 50% to 75% and the porosity of the outer porous layer is 30% to 50%;

the inner porous layer has a higher porosity than that of the diffusion resistor; and as viewed in a plurality of 100 μm×100 μm regions on a scanning electron micrograph of sections of the inner porous layer and the diffusion resistor, a pore diameter greater than a greatest pore diameter $C_{DIF}$ in the regions of the diffusion resistor exists in each of the regions of the inner porous layer.

2. The gas sensor element as claimed in claim 1, wherein the inner porous layer entirely covers the forward end portion of the laminate.

3. The gas sensor element as claimed in claim 2, wherein the gas sensor element is an $NO_x$ sensor element which includes a first pump cell which has a pair of first electrodes disposed on a first solid electrolyte layer located internally and externally of a first measuring chamber and which is adapted to pump oxygen into and out of a gas-to-be-measured that has been introduced into the first measuring chamber, and a second pump cell which has a pair of second electrodes provided on a second solid electrolyte layer located internally and externally of an $NO_x$ measuring chamber in communication with the first measuring chamber and in which a second pumping current flows between the pair of second electrodes according to an $NO_x$ concentration in a gas having adjusted oxygen concentration and flowing from the first measuring chamber into the $NO_x$ measuring chamber; and the at least one cell is the first pump cell, and the at least one measuring chamber is the first measuring chamber.

4. A gas sensor comprising a sensor element for detecting concentration of a particular gas component in a gas-to-be-measured, and a housing for holding the sensor element, wherein the sensor element is the gas sensor element as claimed in claim 2.

5. The gas sensor element as claimed in claim 1, wherein the gas sensor element is an $NO_x$ sensor element which includes a first pump cell which has a pair of first electrodes disposed on a first solid electrolyte layer located internally and externally of a first measuring chamber and which is adapted to pump oxygen into and out of a gas-to-be-measured that has been introduced into the first measuring chamber, and a second pump cell which has a pair of second electrodes provided on a second solid electrolyte layer located internally and externally of an $NO_x$ measuring chamber in communication with the first measuring chamber and in which a second pumping current flows between the pair of second electrodes according to an $NO_x$ concentration in a gas having adjusted oxygen concentration and flowing from the first measuring chamber into the $NO_x$ measuring chamber; and the at least one cell is the first pump cell, and the at least one measuring chamber is the first measuring chamber.

6. A gas sensor comprising a sensor element for detecting concentration of a particular gas component in a gas-to-be-measured, and a housing for holding the sensor element, wherein the sensor element is the gas sensor element as claimed in claim 5.

7. A gas sensor comprising a sensor element for detecting concentration of a particular gas component in a gas-to-be-measured, and a housing for holding the sensor element, wherein the sensor element is the gas sensor element as claimed in claim 1.

8. The gas sensor element of claim 1, wherein the diffusion resistor has a higher porosity than that of the outer porous layer.

9. The gas sensor element of claim 1, wherein the diffusion resistor has a porosity of 40% to 55%.

10. The gas sensor element of claim 1, wherein the diffusion resistor has a porosity of 40% to 55% that is higher than that of the outer porous layer.

* * * * *